United States Patent [19]
Hermann et al.

[11] Patent Number: 5,630,822
[45] Date of Patent: May 20, 1997

[54] LAPAROSCOPIC TISSUE REMOVAL DEVICE

[75] Inventors: George D. Hermann, Los Gatos; Kenneth H. Mollenauer, Santa Clara; Michelle Y. Monfort, Los Gatos; Timothy J. Ryan; Shigeru Tanaka, both of Palo Alto, all of Calif.

[73] Assignee: General Surgical Innovations, Inc, Palo Alto, Calif.

[21] Appl. No.: 376,027

[22] Filed: Jan. 20, 1995

Related U.S. Application Data

[63] Continuation-in-part of Ser. No. 226,386, Apr. 12, 1994, abandoned, which is a continuation of Ser. No. 87,214, Jul. 2, 1993, abandoned.

[51] Int. Cl.$^6$ .................................................. A61B 17/22
[52] U.S. Cl. .................................... 606/114; 606/127
[58] Field of Search ................................ 606/151, 127, 606/205–207, 198, 114

[56] References Cited

U.S. PATENT DOCUMENTS

| | | | |
|---|---|---|---|
| 4,873,978 | 10/1989 | Ginsburg . | |
| 5,102,415 | 4/1992 | Guenther et al. | 656/159 |
| 5,143,082 | 9/1992 | Kindberg et al. | 606/151 |
| 5,176,687 | 1/1993 | Hasson et al. | 606/127 |
| 5,190,555 | 3/1993 | Wetter et al. | 606/127 X |
| 5,190,561 | 3/1993 | Graber | 606/127 |
| 5,190,595 | 3/1993 | Wetter et al. | 606/127 |
| 5,192,284 | 3/1993 | Pleatman | 606/127 |
| 5,217,468 | 6/1993 | Clement | 606/127 |
| 5,312,417 | 5/1994 | Wilk | 606/127 |
| 5,330,483 | 7/1994 | Heaven et al. | 606/127 |
| 5,368,597 | 11/1994 | Pagedas | 606/127 X |
| 5,370,647 | 12/1994 | Graber et al. | 606/127 |

FOREIGN PATENT DOCUMENTS

| | | | |
|---|---|---|---|
| 2057636 | 3/1972 | Germany | 606/127 |
| 2057636 | 3/1992 | Germany | 606/127 |

*Primary Examiner*—Michael H. Thaler
*Attorney, Agent, or Firm*—Lyon & Lyon LLP

[57] ABSTRACT

A laparoscopic tissue removal device for use by fingers of a hand comprising an elongate tubular member with proximal and distal extremities and having a bore extending therethrough. An elongate tubular member has an outer diameter and an elongate tubular sheath is formed of a tubular woven braid material having proximal and distal extremities. A length extends between the proximal distal extremities. The elongate tubular sheath has a passage extending from the proximal extremity to the distal extremity. The tubular woven braid material of the elongate tubular sheath has an initial configuration and an open weave construction permitting the elongate tubular sheath to enlarge beyond its initial diameter to a diameter substantially greater than the initial diameter. The proximal extremity of the elongate tubular sheath is secured to the elongate tubular member. The distal extremity of the elongate tubular sheath has a distal portion capable of assuming an outwardly flared configuration which when free has an open end that has a diameter substantially greater than the initial diameter of the passage extending through the elongate sheath. An outer sleeve is slidably mounted on the elongate tubular member and is movable into a position so that it extends over the elongate tubular sheath. The initial diameter of the elongate tubular sheath is determined with respect to the outer sleeve when the elongate tubular member is free of the outer sleeve. The tubular woven braid construction of the elongate tubular sheath permits the elongate tubular sheath to receive and retain therein tissue having a diameter greater than the diameter of the bore whereby when the elongate tubular sheath is drawn into the outer sleeve, the tissue is reduced in diameter so that the tissue can be withdrawn into the outer sleeve.

14 Claims, 4 Drawing Sheets

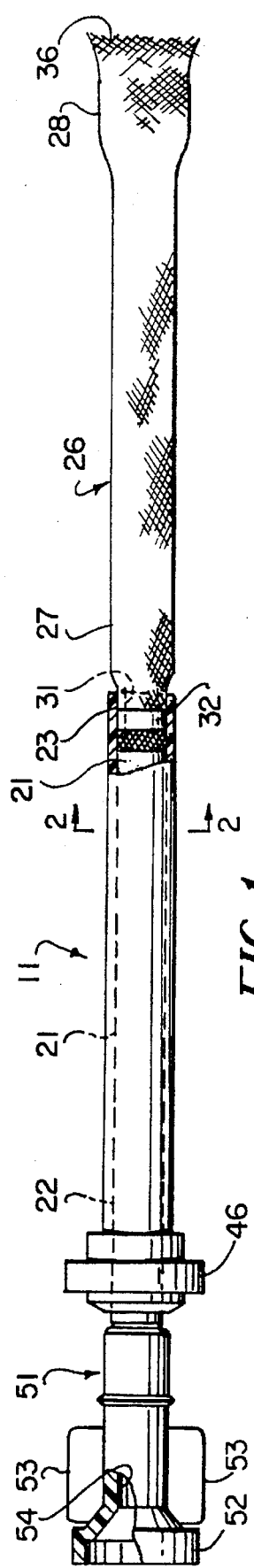
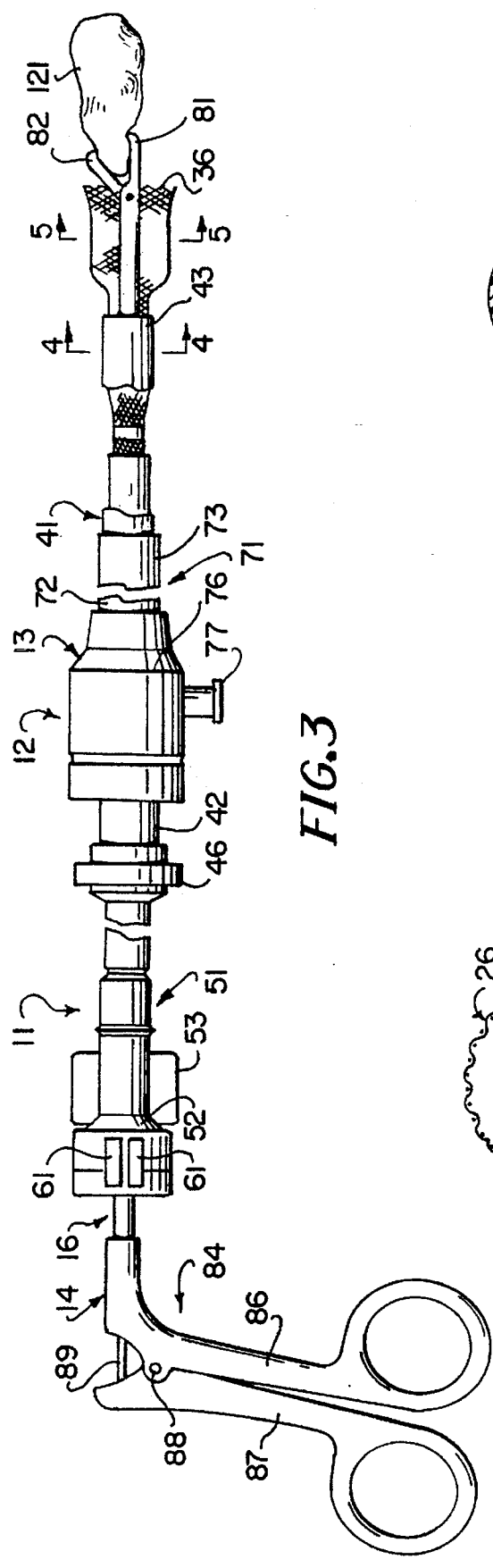
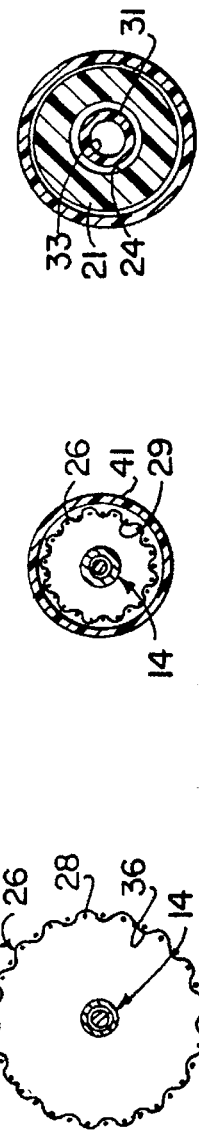
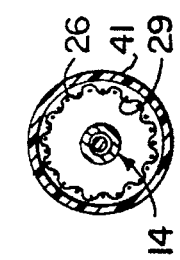
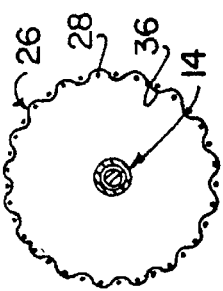

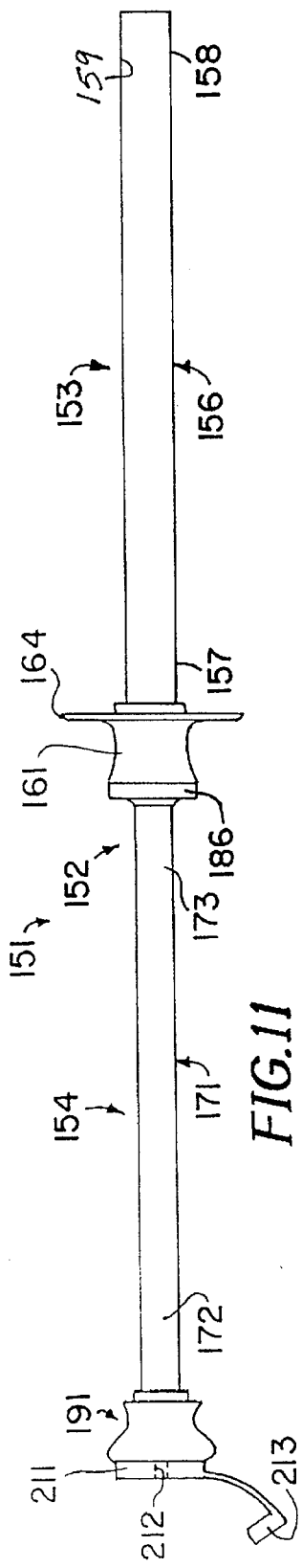
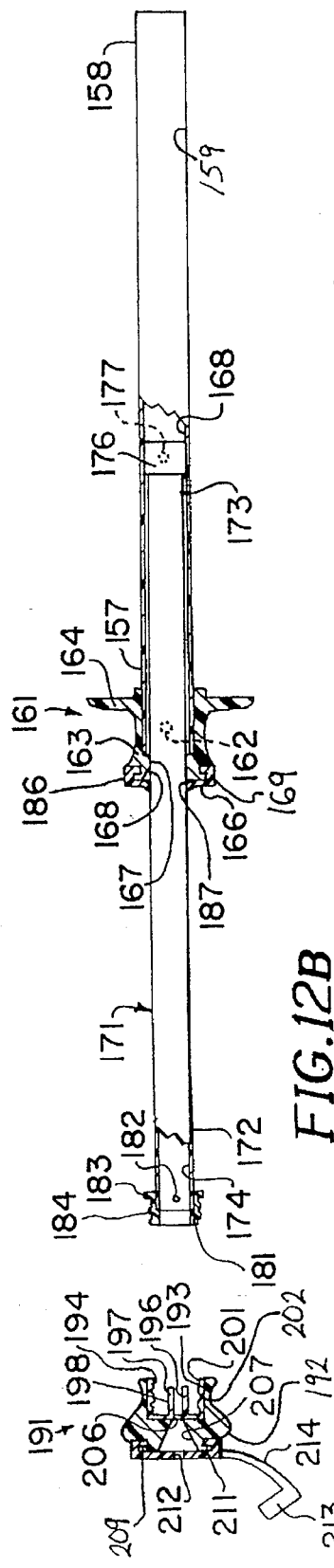
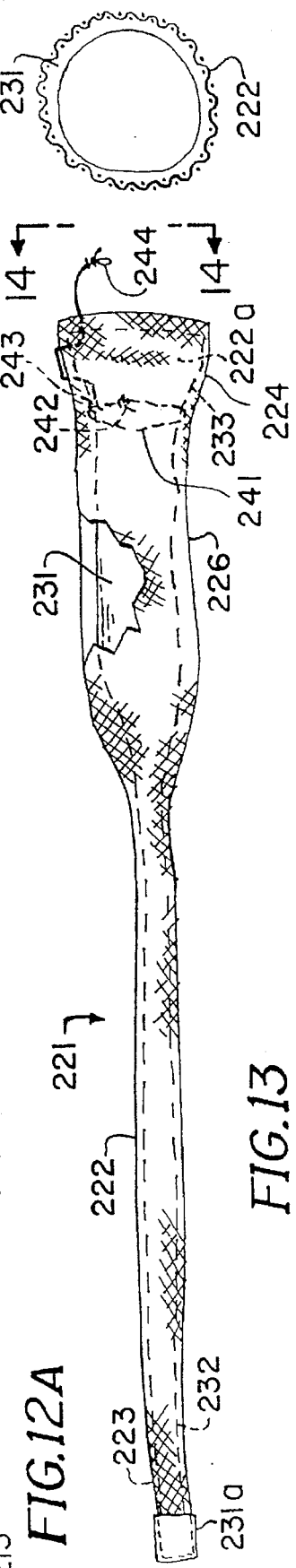
FIG.11
FIG.12A
FIG.12B
FIG.13
FIG.14

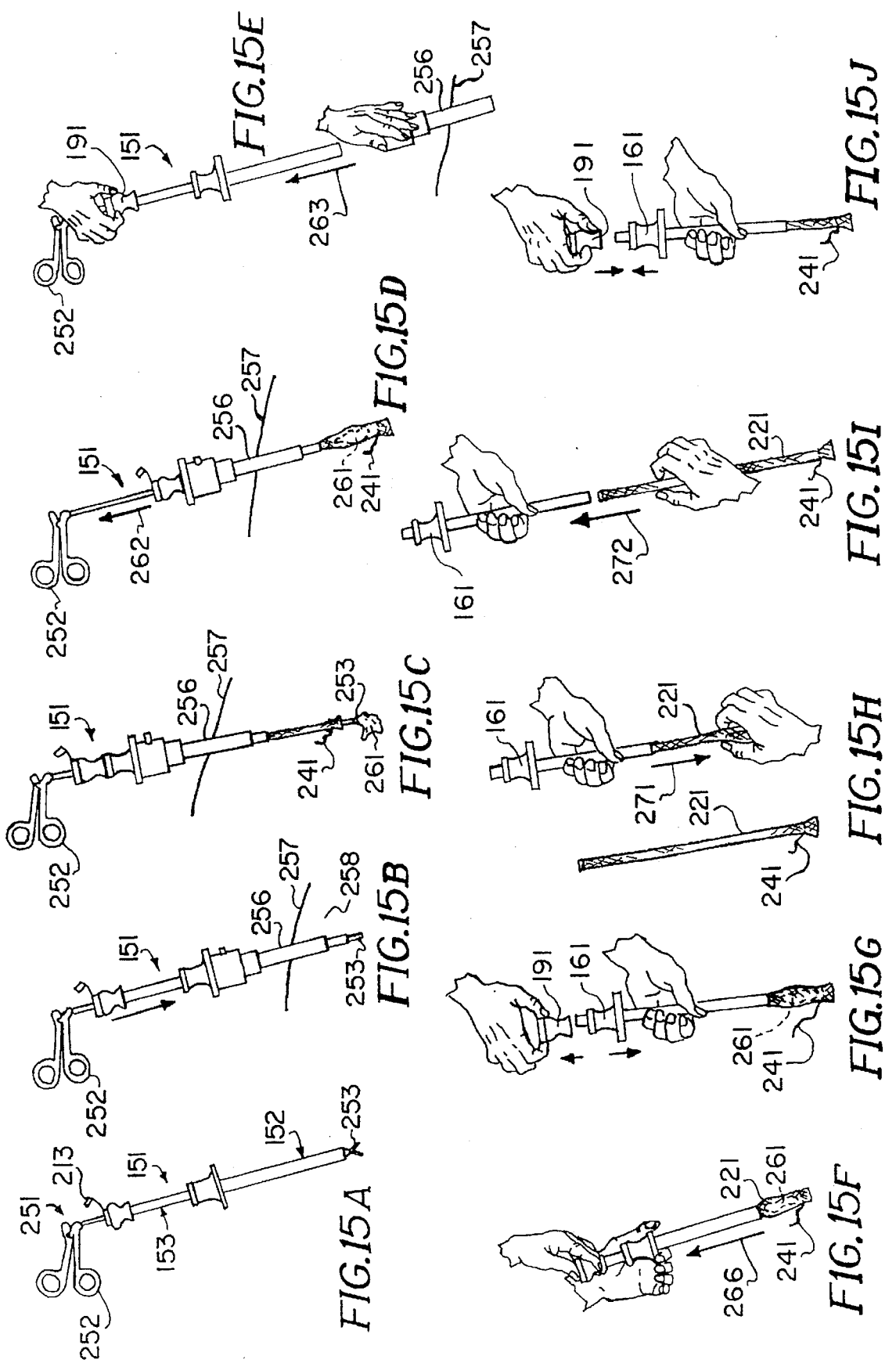

LAPAROSCOPIC TISSUE REMOVAL DEVICE

This application is a continuation-in-part of application Ser. No. 08/226,386 filed on Apr. 12, 1994, now abandoned which is a continuation of application Ser. No. 08/087,214 filed on Jul. 2, 1993, now abandoned.

In a number of laparoscopic procedures, it is desirable to remove tissue during the procedure. In many cases, this tissue is of a size which is greater than that which can be passed through a conventional introducer such as gallbladders, lymph nodes and appendices and other masses of tissue. In the past, it has been the practice, when the tissue is too large to be brought through a conventional introducer, to remove the introducer and enlarge the incision or slit through which the trocar or introducer has been placed to permit removal of such larger body tissues. Other procedures have merely used larger size introducer tubes as for example up to 30 millimeters in diameter to make it possible to remove larger masses of tissue. Switching to a larger tube requires time and additional expense and also increases the size of the incision in the patient. There is therefore need for new and an improved laparoscopic tissue removal device, an assembly thereof and a method which overcomes the above named disadvantages.

In general, it is an object of the present invention to provide a laparoscopic tissue removal device, an assembly thereof and a method which facilitates the removal of relatively large masses of tissue through a conventional size introducer utilized in a laparoscopic procedure.

Another object on the invention is to provide a device, assembly and method of the above character in which a mesh material is utilized to do a draw down and elongate the mass of tissue to thereby reduce the diameter of the same so that it can be withdrawn through a conventional size introducer.

Another object of the invention is to provide a device, assembly and method of the above character in which the mass of tissue can be enclosed within the mesh material to prevent its escape during withdrawal.

Another object of the invention is to provide a device, assembly and method of the above character which includes an permeable bag into which the tissue can be withdrawn and the bag tightly sealed to prevent the seeding of cancer cells in the event they are present in the tissue being removed.

Another object of the invention is to provide a device, assembly and method of the above character in which the entire bag and its contents can be removed as a unit and shipped to a laboratory for analysis.

Another object of the invention is to provide a device, assembly and method of the above character in which a separable handle is utilized which can be reused.

Another object of the invention is to provide a device, assembly and method of the above character in which the mass of a tissue can be readily compressed and withdrawn.

Another object of the invention is to provide a device, assembly and method of the above character in which a taught line hitch is utilized for closing off the bag ensure that the bag is sealed.

Additional objects and features of the invention will appear from the following description in which the preferred embodiments are set forth in detail conjunction with the accompanying drawing.

FIG. 1 is a side elevational view partially in cross-section of a laparoscopic tissue removal device incorporating the present invention.

FIG. 2 is a cross-sectional view taken along the line 2—2 of FIG. 1.

FIG. 3 is a side elevational view partially in cross-section of an assembly incorporating the present invention which includes the laparoscopic tissue removal device as a part thereof.

FIG. 4 is a cross-sectional view taken along the line 4—4 of FIG. 3.

FIG. 5 is a cross-sectional view taken along the line 5—5 of FIG. 3.

FIG. 11 is a side elevational view of another embodiment of a laparoscopic tissue removable device incorporating the present invention.

FIG. 12A is a cross sectional view of the screw cap utilized in the laparoscopic tissue removal device as shown in FIG. 11.

FIG. 12B is a cross sectional view of the tubular assembly forming a part of the laparoscopic tissue removal device as shown in FIG. 11.

FIG. 13 is a side elevational view of a container assembly utilized in the laparoscopic tissue removal device as shown in FIG. 11.

FIG. 14 is an end elevational view taken along the line 14—14 of FIG. 13.

FIGS. 15A through 15J are illustrations depicting the manner in which the laparoscopic tissue removal device shown in FIGS. 11 through 15 is utilized in performing the method of the present invention.

Figure 6:
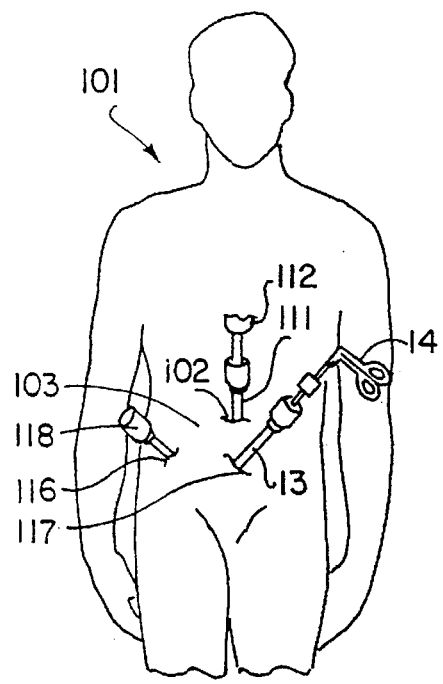
FIG. 6 is a plan view of a human being on which a laparoscopic procedure is being performed utilizing the laparoscopic tissue removal device and assembly incorporating the present invention for removal of a lymph node.

In general, the laparoscopic tissue removal device incorporating the present invention is comprised of a elongate tubular member having proximal and distal extremities and having a bore extending therethrough. An elongate sheath is provided which is formed of a tubular braid material having proximal and distal extremities and having a passage extending therethrough from the proximal extremity to the distal extremity. Means is provided for securing the proximal extremity of the sheath to the distal extremity of the elongate tubular member. The distal extremity of the sheath has a conformation so that in a free state it assumes an outwardly flared configuration which has an open end.

More in particular, as shown in the drawings, the laparoscopic tissue removal device 11 is adapted to be disposed within an assembly 12 that includes an introducer 13 and a grasper 14. A conventional pneumostatic valve 16 is provided on the tissue removal device 11 to form a seal around the grasper 14.

The laparoscopic tissue removal device 11 consists of a elongate rigid tubular member 21 having proximal and distal extremities 22 and 23 and having a bore 24 extending therethrough.

An expandable sheath 26 is provided which has proximal and distal extremities 27 and 28 and having a passage 29 extending through. The expandable sheath 26 is formed of a tubular woven material such as a braid material and has a diameter which is no greater than the outer diameter of the elongate tubular member 21. Suitable means is provided for securing the proximal extremity 27 of the sheath 26 to the distal extremity 23 of the elongate tubular member 21 and consists of a short sleeve 31 of a reduced diameter which is fixed within the distal extremity of the elongate tubular member 21 by suitable means such as an adhesive (not shown). The short sleeve 31 extends distally of the distal extremity 23 of the elongate tubular member 21 and has the proximal extremity 27 of the expandable sheath 26 secured thereto by an adhesive band 32. The short sleeve 31 has a bore 33 extending therethrough which is in communication with the bore 24 in the elongate tubular member 21 and the passage 29 of the expandable sheath 26.

The elongate tubular member 21 can be formed of a suitable plastic such as GE GR1110 polycarbonate and can have a suitable outside diameter such as 8 millimeters so that it can be utilized in connection with a device 11 that can fit within the 10–11 millimeter inside diameter of a conventional introducer 13. It can have a wall thickness of ½ millimeter to provide a bore 24 having a diameter of 7 millimeters. The short sleeve 31 can have a bore 33 having a diameter of 6 millimeters.

The expandable sheath can be formed of a suitable tubular braid material as for example sleeving supplied by Bentley Harris under the trademark Expando PT. It is very flexible and has an open weave construction which enables is to enlarge to up to three times its own initial diameter. The distal extremity 28 of the sheath 26 is formed into a bell-shaped configuration. This bell-shaped configuration can be readily obtained by heat forming over a mandrel. Thus a mandrel (not shown) of the desired shape can be used. The distal extremity 28 is fitted over the mandrel and then heated to a suitable temperature as for example a temperature substantially above 125° C. The distal extremity 28 is then cooled while the mandrel is still in place to cause a distal extremity 28 to permanently retain the desired bell shape or in other words to have a memory of this expanded bell-shaped configuration which is provided with an open end 36.

If it is desired that the expandable sheath 26 be sealed so that it will not leak air or a gas, a suitable elastomer can be impregnated into the braid to close the open pores between the braid. This will provide an additional memory in the expandable sheath 26 which will cause it to want to return to its original shape when it is expanded or stretched. An elastomer suitable for this use is MED2-6640 supplied by McGhan Nusil of Carpenteria, Calif.

The bell-like distal extremity 28 can have a suitable length as for example 2.5 centimeters and a diameter at the open end 36 of approximately 2.5 centimeters. The expandable sheath 26 can have a overall length of approximately 15 centimeters.

An outer sleeve 41 is disposed over the elongate tubular member 21 and has a proximal extremity 42 and a distal extremity 43. It is provided with a bore 44 which extends from the proximal extremity 42 to the distal extremity 43. A collar 46 is secured to the proximal extremity 42 by a suitable means such as an adhesive. The outer sleeve 41 is formed of a suitable material such as a transparent plastic and is slidably mounted on the elongate tubular member 21 so that it can be moved longitudinally of the elongate tubular member 21 by fingers of the hand grasping the collar 46.

A fitting 51 is mounted on the proximal extremity 22 of the flexible elongate tubular member 21 and is secured thereto by suitable means such as an adhesive. The fitting 51 is provided with a flared proximal extremity 52 and diametrically extending butterfly type wings 53 which are adapted to be grasped by the hand to cause rotation of the elongate tubular member 21. The outer sleeve 41 has a length so that when the collar 46 is disposed adjacent the fitting 51, the distal extremity 43 of the outer sleeve 41 extends slightly beyond the distal extremity 23 of the elongate tubular member 21 and thus extends over the expandable sheath 26. The fitting 51 has a bore 54 extending therethrough which is in communication with the bore 24 provided in the flexible elongate tubular member 21.

The valve 16 which is adapted to fit on the end of the fitting 51 is of a conventional type and can be of an iris type which provides a relatively large opening for tools to be inserted into and removed therefrom. It also permits the removal of large masses of tissue as hereinafter described. The valve 16 can be provided with operating members 61 to permit the same to be opened to facilitate insertion of tools and/or removal of large masses of tissue as hereinafter described.

The assembly 12 in which the device 11 is used includes the introducer 13 which as hereinbefore described is of a conventional type. It for example can be comprised of a tubular member 71 having an inside diameter as for example 10 to 11 millimeters and having proximal and distal extremities 72 and 73. A housing 76 is secured to the proximal extremity 72 by suitable means such as an adhesive (not shown). A Luer-type fitting 77 is mounted on the housing 76. The housing 76 is formed so that it is adapted to by being received in or engage the housing 76.

The grasper 14 also is of a conventional type and is provided with jaws 81 and 82 mounted on a shaft 83 carried by a handle mechanism 84 consisting of scissors-like handles 86 and 87 which are pivotally mounted at 88 for moving an actuating rod 89.

Operation of the laparoscopic tissue removal device 11 in conjunction with the assembly 12 may now be briefly described as follows. Let it be assumed that it is desired to perform a laparoscopic procedure on a human 101 as shown in FIG. 6 of the drawings in which it is desired to remove a lymph node from a human to ascertain the stage of prostatic cancer which has been discovered. Also let it be assumed that an incision 102 has been made in the abdominal wall 103 and that a properitoneal space 104 has been created between the abdominal wall 103 and the peritoneum 106 in a manner described in co-pending application Ser. No. 07/893,988, filed Jun. 2, 1992 and that the space 104 has been insufflated by a gas. Also let it be assumed that an introducer 111 has been placed in the umbilicus 102 and that a scope 112 of conventional type has been placed in the introducer 111 for viewing the properitoneal space 104.

Figure 7:
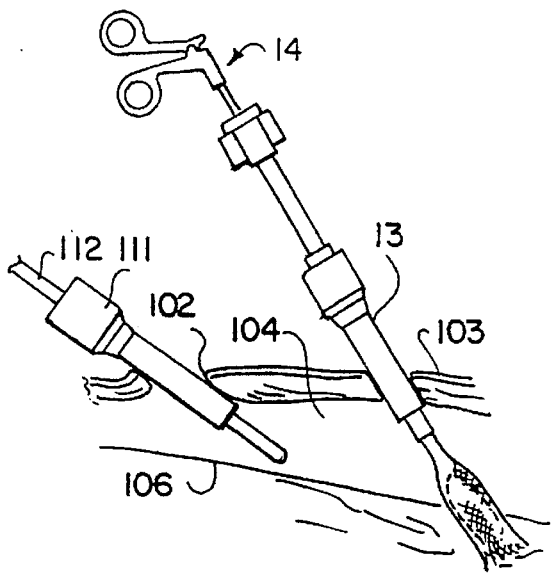
FIG. 7 is a cross-sectional view of the laparoscopic procedure being performed in FIG. 6.

Also let it be assumed that other incisions or cuts 116 and 117 have been made in the abdominal wall 103 and other introducers placed therein as for example another introducer 118 as well as the introducer 13 utilized in the assembly 12 in connection with the present invention. Let it be assumed that it is desired to retrieve a lymph node which has been dissected. The laparoscopic tissue removal device 11 is in a position in which the bell-shaped distal extremity 28 of the expandable sheath 26 is disposed within the outer sleeve 41 so that it is compressed within the outer sleeve and is enclosed within the outer sleeve. The device 11 can then be introduced through the introducer 13 so that the distal extremity of the outer sleeve 41 extends into the properitoneal space 104 as shown in FIG. 7. After the distal extremity 43 has been advanced to the desired position, the collar 46 is grasped with one hand while holding the fitting 51 in the other hand and retracting the collar 46 to bring with it the outer sleeve 41 to gradually expose the distal extremity 28 of the expandable sheath 26 permitting it to expand to its normal expanded bell-shaped configuration with an open end 36.

Figure 8:
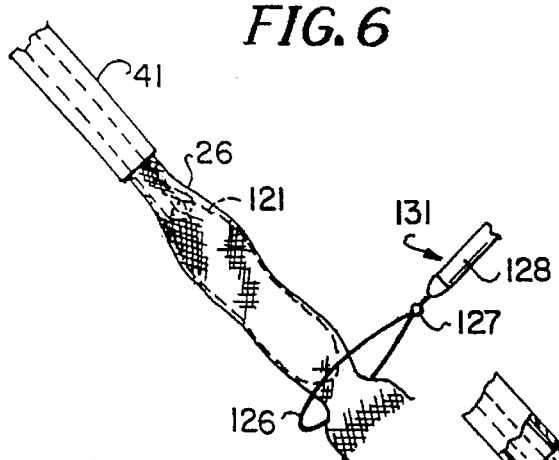
FIG. 8 is a partial isometric view showing a ligature in the form of a pre-knotted suture being used for ligating the end of a mesh closure having a mass of tissue to be removed therein.
Figure 9:
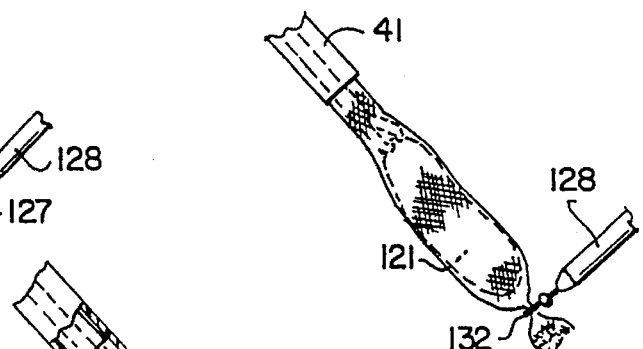
FIG. 9 is an isometric view similar to FIG. 8 but showing the pre-knotted suture used for ligating the open end of the mesh enclosure being closed off.

The grasper 14 with its jaws 81 and 82 in a closed position can then be inserted through the valve 16 and into the fitting 51 and thence into the bore 24 of the elongate tubular member 21. It is then advanced through the same bore 33 and the short sleeve 31 and into the passage 29 provided in expandable sheath 26 until the jaws 81 and 82 extend beyond the distal extremity of the bell-shaped portion of the expandable sheath 26. The tissue removal or retrieval device 11 is then positioned so that the open end 36 of the bell-shaped distal extremity 28 is adjacent the mass of tissue 121 as for example a lymph node to be removed from the properitoneal space. While viewing the procedure under the scope 112, the surgeon doing the removal operates the handles 86 and 87 to close the jaws to grasp the mass of tissue 121. As soon as the tissue 121 has been grasped, the surgeon moves the grasper 14 proximately relative to the tissue removal device 11 to drag or pull a portion of the tissue mass 121 into the open end 36 of the bell-shaped distal extremity 28. If the bell-shaped distal extremity 28 is inadequate to receive the entire length of the mass of tissue 121, the outer sleeve 41 can be further retracted to expose an additional length of the expandable sheath 26 until there is a length at least great enough to accommodate the entire length of the mass of tissue 121. Also other conventional laparoscopic grasping tools can be used to push the mass of tissue into the flared end of the tissue removal device. Thus as shown in FIG. 8, the grasper can be utilized to bring the mass of tissue 121 completely within the confines of the expandable sheath 26. As shown in FIG. 8, the mass of tissue 121 can have a size which is substantially greater than the initial size of the outer sleeve 41. This greater size can be readily accommodated by the expandable sheath 26 because of its capability to expand by more than three times its original size.

Figure 10:
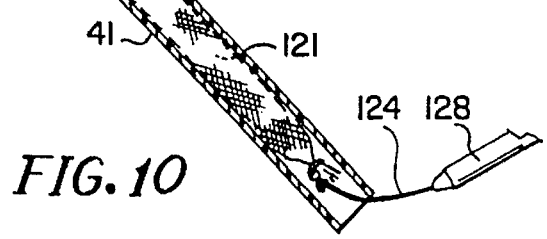
FIG. 10 is a view, similar to FIG. 9 showing the mass of tissue being enclosed within the mesh material and being withdrawn through a conventional size introducer.

In order to prevent escape of the mass of tissue 121 from the expandable sheath 26 after it has been brought therein by the grasper 14, the distal extremity of the bell-shaped extremity 28 can be closed by the use of a pre-knotted suture 126 that is provided with a knot 127 which can be pushed to close the loop 126 by the use of a pusher rod 128 of a conventional ligation device 131. As soon as the loop 126 has been closed about the distal extremity of the distal bell-shaped portion 28, a ligature 132 is formed. With the ligation device 132 still in place through one of the introducers as for example introducer 118, the grasper 14 can be held stationary by the surgeon while the other hand of the surgeon engages the collar 46 to move the outer sleeve 41 distally to progressively cause a reduction in a diametrical direction of the mass of tissue 121 and at the same time a progressive elongation of the tissue 121 so that the tissue 121 can be moved into the interior of the outer sleeve 41 until it is completely enclosed therein as shown in FIG. 10. Alternatively, the grasper 14 can be moved and the outer sleeve 41 held stationary to pull the tissue 121 into the outer sleeve 41 to cause the same progressive reduction and elongation of the tissue 121.

After this has been accomplished, the entire tissue removal device 11 can be removed from the assembly 12 carrying with it the grasper 14. During this removal, the suture 124 can be permitted to extend through the pusher rod 128. After the mass of tissue 121 is outside of the body, the suture 124 can be cut to release the suture 124 and to permit it to be withdrawn with the pusher rod 128 from the other introducer 118. After the tissue removal device 11 is out of the body, the mass of tissue 121 therein can be discharged by pushing the grasper 14 in a distal direction to move the mass of tissue 121 out of the distal extremity of the outer sleeve 41. Also the mass of tissue can be placed in a containment sack and this sack with the mass therein can be placed in the bell-shaped distal extremity of the tissue removal device and removed in the same manner as hereinbefore described.

If additional masses need be removed, the same procedure can be repeated utilizing another tissue removal device 11 or by utilizing the same tissue removal device after the mass of tissue 121 has been removed therefrom. After all of the desired tissue has been removed from the abdominal cavity, the cavity 104 can be deflated, the introducers removed and the incisions 102, 117 and 116 closed in a suitable manner such as by the use of sterile strips.

From the foregoing it can be seen that there has been provided a laparoscopic tissue removal or retrieval device 11 and an assembly utilizing the same and a method for permitting removal of relatively large masses of tissue in the form of body parts such as a gallbladder, lymph nodes and the like. The device makes it possible to retrieve relatively large masses of tissue by bringing at least a portion of the tissue into a bell-shaped distal extremity of the expandable sheath by physically drawing the tissue therein by use of a grasper and then progressively bringing the tissue into the expandable sheath and closing the expandable sheath around the tissue. The tissue can then be necked down to be compressed or reduced circumferentially while permitting expansion longitudinally to bring the mass of tissue down to a size so that it is unnecessary to provide larger diameter introducers or to make a larger incision to remove a body part. This technique also makes it possible to remove larger masses of tissue without the necessity of a correspondingly larger incision. This minimizes trauma to the patient and reduces the possibility of scar tissue forming. The bell-shaped opening provided in the distal extremity of the expandable sheath makes it possible to funnel tissue into the same and to permit the tissue to be readily retracted into expandable portions of the expandable sheath.

Another embodiment of a laparoscopic tissue removal device 151 is shown in FIGS. 11 through 14. The laparoscopic tissue removal device 151 consists of a composite tubular assembly 152 which is comprised of a first or outer tubular assembly 153 and a second or inner tubular assembly 154. The first or outer tubular assembly consists of a tubular member 156 which is provided with proximal distal extremities 157 and 158 respectively. The tubular member 156 can have a suitable length as for example 6.75" and can have an outside diameter of approximately 0.430" with a wall thickness of 0.020". The tubular member 156 is formed of a suitable material such as epoxy impregnated glass braid of the type supplied by Polygon International of Walkerton, Ind. The tubular member 156 has a bore 159 extending therethrough from the proximal extremity to the distal extremity.

The first or outer tubular assembly 153 is provided with a handle 161 which is molded of a suitable material such as a white polycarbonate. The proximal extremity 157 of the tubular member 156 is provided with a plurality of circumferentially spaced apart holes 162 which are adapted to receive a portion of the material which forms the handle or knob 161 so that the handle or knob 161 is retained in a fixed position on the proximal extremity of the tubular member 156. The handle 161 is provided a cylindrical body 163 that is provided with an outwardly radially extending flange 164 which is adapted to be grasped by the fingers of a hand. The proximal extremity 157 is seated against an annular shoulder 166 which overlies the bore 159. The bore 159 opens into a short bore 167 which opens into an outwardly tapered bore 168. An outwardly facing annular recess 169 is provided on the exterior surface of the body 163 which is utilized for a purpose hereinafter described.

The second or inner tubular assembly 154 is coaxially and slidably mounted within the outer tubular assembly 153 and consists of an elongate tubular member 171 having proximal and distal extremities 172 and 173. The tubular member 171 can have a suitable length as for example 7.25" and can have an outside dimension of 0.375" with a wall thickness of approximately 0.020" to provide a bore 174 extending from the proximal extremity 172 to the distal extremity 173. An outer cylindrical collar 176 is mounted on the distal extremity 173 of the tubular member 171. It is formed of a suitable material such as a polycarbonate and is secured to the distal extremity 173 by suitable means such as molding the collar 176 onto the distal extremity and having material flow into circumferentially spaced apart holes 177 provided in the tubular member 171. The exterior dimensions of the collar 176 are such that it can travel within the bore 168 of the tubular member 156 but will not clear the shoulder 166 provided in the handle 161 for a purpose hereinafter described.

A collar 181 is mounted on the proximal extremity of the tubular member 171 and is also formed of a molded material such as a polycarbonate and is retained thereon by having material forming the collar 181 extend into circumferentially spaced apart holes 182 provided in the proximal extremity 172. The collar 181 is provided with a radially extending flange 183 and external helical threads 184 formed integral with the collar.

Means is provided for establishing a fluid tight seal between the first and second tubular assemblies 152 and 153 during relative slidable movement between the same and consists of a membrane type seal 186 which is provided with a hole 187 therethrough in axial alignment with the bore 159. The hole 187 is sized so that it can receive the tubular member 171 to maintain a fluid tight seal while permitting axial movement of the member 171 longitudinally of the bore 159.

A twist cap 191 is adapted to be threadedly mounted on the externally threaded collar 181 and consists of a body 192 formed of a suitable material such as molded polycarbonate of the type hereinbefore described. The body 192 is provided with a large cylindrical recess 193 which has an insert 194 mounted therein and retained therein by suitable means such as an adhesive. The insert 194 is also formed of a suitable material such as a clear polycarbonate. The insert 194 has a bore 196 extending therethrough which is circumscribed by a cylindrical wall 197 to form a protrusion having an inwardly and forwardly extending tapered surface 198. An annular recess 201 formed in the insert 194 circumscribes the tapered surface 198 and has an inner cylindrical surface 202 which has a helical thread formed therein which are adapted to mate with the helical thread 184 provided on the collar 181.

The body 192 of the twist cap 191 is provided with a bore 206 which is in registration with the bore 196 in the insert 194. The bore 206 opens into a tapered opening 207. The exterior surface of the body 192 is provided with an annular recess 209 which faces outwardly and has mounted therein a membrane type seal 211 which extends across the tapered opening 207. The seal 211 has a centrally disposed hole 212 therein which is in alignment with the bore 206 and the bore 196. The hole 212 is sized so it is adapted to permit instruments to be passed therethrough as hereinafter described while still maintaining a fluid tight seal therewith. A cylindrical plug 213 formed of the same elastic silicone material as the membrane tight seal 211 is adapted to be inserted into the hole 212 to plug the same to prevent the escape of fluids therethrough. The plug 213 as shown can be attached to and formed of a part of the membrane seal 211 by a flexible elongate member 214 formed integral with the membrane seal 24.

The laparoscopic tissue removal device 151 also includes a tissue container assembly 221. The tissue container assembly 221 as shown in FIG. 13 consists of an elongate tubular sheath or a braided open mesh tube 222 formed of a suitable material such as a polyester. The tube 222 is cut to a suitable length as for example 16" and typically has a suitable diameter such as ¼" when stretched. The tube 222 has proximal and distal extremities 223 and 224 respectively. The tube 222 can then be inserted over a mandrel so that it is expanded to the desired size and then one end of the braided tube can be cut and the strands welded. The distal end of the tube 222 is then folded inwardly a suitable amount as for example ¼" to provide a folded-over portion 222a. This folded over distal end 224 is then placed over the mandrel and then the braided tube 222 is pulled on the other smaller or proximal end 223 while holding the distal end 224 on the mandrel with the other hand. The braided tube 222 at the small proximal end 223 is then cut off with a heat knife. The tube 222 while positioned on the mandrel is then heated in a suitable manner as for example in an oven for a suitable period of time as for example 20 minutes plus or minus 5 minutes at 110° C. plus or minus 10° C. After the braided tube 222 has been heated for this period of time, it is removed from the oven and permitted to cool for a period of time from 10 minutes up to 15 minutes. The braided tube 222 is then removed from the mandrel so that there is provided a braided tube 222 which has enlarged flared bell-shaped end portion 226 in which the distal end 224 is reinforced by the folded-over portion 222a.

The tissue container assembly 221 also includes an inner impervious elongate liner 231. The liner 231 is provided with proximal and distal extremities 232 and 233 respectively. The liner 231 is formed of a suitable impervious material such as a urethane sheet having a wall thickness of for example 0.0015". By way of example, the urethane sheet can be cut into strips and then heat sealed in a sealer to provide an inner liner which has a cylindrical configuration having a diameter which can be expanded to 1–¼". The folded over lip 222a of the braided tube 222 is then unfolded outwardly The inner liner 231 after it has been cut to the appropriate length is retained on a mandrel and inserted started with its small end through the large bell-shaped portion 226 and is moved until the small proximal end 223 extends out of the proximal end 223 of the braided tube 222. A portion 231a of the inner liner 231 is folded over the proximal extremity 223 of the braided tube 222 and is heat sealed thereabout. The distal extremity of the inner liner 231 is then heat sealed at the distal extremity of the braided tube 222. The end 222a is then refolded inwardly over the distal extremity of the inner liner 231.

A drawstring 241 is provided for closing the distal extremity of the inner liner 231. The drawstring 241 is formed from a conventional suture material as for example a braided polyester of 2/0 gauge. To form the drawstring, a suture is cut to a suitable length as for example 7" and an over-hand knot 242 is tied into one end of the same. Any excess is cut off beyond the square knot at that end. The suture end without the knot is placed through an eye of a blunt needle (not shown). The needle is passed radially through the braided tube 222 at approximately ½" from the distal extremity 224 and is passed circumferentially around the distal extremity of the inner liner 231 in a region where the inner liner is free of the distal extremity 224 of the braided tube 222 so that the suture circumferentially circumscribes approximately 180° of the outside of the inner liner 231 and is then passed through an opening in the braid and then is brought back through the next adjacent opening in the braid and then around the outside of the inner liner for another 180° and then through the same opening in the braid through which the suture had originally been passed and the needle is removed. Using the suture end with the square knot 242 therein a slip knot is tied around the free end of the suture extending beyond the braided tube by placing two throws around the other portion of the suture. After the slip knot 243 has been formed, the free end can again be placed through the needle (not shown). It should be appreciated if desired the needle can be left in place on the free end while the slip knot 243 is being tied. The needle is then passed through the braided tube 222 at a point approximately half way between the slip knot 243 and the distal extremity of the braided tube 222 then out through the distal extremity of the braided tube 222. An end knot 244 is tied onto the free end of the suture by tying several loops into it to form the end knot so that it is of a size so that it can be readily grasped by the fingers of the human hand or with an instrument. The slip knot 243 is one of a class of sliding knots which cinch up easily and resist opening of the noose after tightening.

Operation and use of the laparoscopic tissue removal device 151 may now be briefly described in connection with the illustrations shown in FIGS. 15A through 15J. Typically the device 151 will be utilized in conjunction with other endoscopic instruments to remove various tissues such as clots, stones, organs or specimens (e.g. biopsies). The device 51 is designed so that it is compatible with standard endoscopic access cannulas and instruments (e.g. grasping and biopsy forceps). Typically, the device 151 will be shipped from the manufacturer with the tissue container 271 mounted within the first or outer tubular member 153 and the second or inner tubular assembly 154 by securing the proximal extremity of the braided tube 222 so that it is secured to the proximal extremity 172 of the tubular member 171 and retained therein by the twist cap 191 as hereinafter described. Typically, the inner tubular assembly 153 will be slidably moved to its most contracted position with respect to the outer tubular assembly 152 so that the distal extremity of the tissue container assembly 221 is disposed outside of the distal extremity 158 of the tubular member 156.

Assuming that is the case when the device 151 is shipped from the manufacturer, the twist cap 191 is grasped by one hand and the other hand is used to grasp the handle 161 to advance the outer tubular assembly 152 so that it completely covers the flexible container assembly 221 and the drawstring 241. As soon as this has been accomplished, a conventional grasping instrument 251 with a conventional scissors-type handle 252 is advanced with its jaws 253 closed through the opening 212 provided in the seal 211 carried by the cap 191. It is then advanced through the bore 196 in the cap 191 and through the bore 174 of the tubular member 171 and the bore 168 of the tubular member 156. As can be seen in FIG. 15A, the grasping instrument 251 typically has a length so that the jaws 253 carried thereby are disposed beyond the distal extremity of the device 151 to permit grasping of tissue as hereinafter described.

Let it be assumed that the laparoscopic procedure is underway and that a conventional cannula 256 with appropriate seals therein has been passed through the skin of the patient as for example the abdominal wall 257 as shown in FIG. 15B so that its distal extremity is disposed in an operating space 258 formed within the patient by insufflation in a manner well known to those skilled in the art. The cannula 256 can be of a conventional size as for example 11 mm or greater. The outer tubular assembly then 152 can be grasped by the hand and advanced through the cannula 256 into the operating space as shown in FIG. 15B.

As soon as the device 151 has been positioned as shown in FIG. 15B, the inner tubular sleeve assembly is pushed inward into the operating space. As the inner tubular assembly 153 is advanced, the distal extremity of the tissue container assembly 221 will be progressively exposed permitting the distal extremity 224 of the braided tube 222 to flare outwardly to its expanded position as shown in FIG. 15C with the drawstring 241 being exposed. The desired tissue specimen 261 can then be grasped by the jaws 253 of the grasping instrument 251 operating the handle 252 as also shown in FIG. 15C. With the tissue 261 being firmly grasped by the jaws 253 of the grasping instrument 251, the grasping instrument 251 is pulled outwardly as indicated by the arrow 262 in FIG. 15D to draw the tissue specimen 261 into the open flared end of the tissue container assembly 221. Because of the braided construction of the tube 222 and the flexibility of the inner liner 231, the braided tube and the inner liner can readily expand to accommodate the specimen.

As soon as the tissue specimen 261 is disposed within the inner liner 231 the drawstring 241 can be grasped by another grasping instrument inserted into the operating space 258 through another cannula (not shown) and can be pulled while holding the grasping instrument 241 and the device 151 to cinch the drawstring 241 into a closed position to close the open end of the inner liner 231 to prevent the escape of the tissue specimen and also to prevent the escape of liquids from the tissue specimen to thereby prevent the spreading of cancerous cells and the like in the event that the tissue specimen may include cancerous tissue. With the drawstring closed, the grasper can release the drawstring.

As soon as this has been accomplished, the inner tubular assembly 154 can be grasped by grasping the cap 191 and while holding the handle 164 in the other hand and retracting the inner tubular assembly 154 to bring with it the tissue container assembly 241 to cause it to be progressively compressed with the tissue therein to cause compression and elongation of the tissue 261 so that the container assembly 241 with the tissue 261 therein can be brought into the confines of the outer tubular assembly 153 until the tissue container assembly 221 is completely disposed within the bore 159 of the outer tubular assembly 153. As soon as this has been accomplished, the entire device 151 can be removed from the cannula 256 as shown in FIG. 15E as indicated by the arrow 263. The tissue container assembly 221 has the capability of receiving relatively large specimens and generally it is possible to compress these specimens so that they can be retracted into the outer tubular assembly 153.

In almost all cases, the tissue specimen being collected can be readily removed through the cannula 256. However in the event that an unduly large tissue specimen is being collected and it is impossible to cause it to be compressed sufficiently to be withdrawn into the outer tubular assembly 154, the tissue removal device 151 along with the cannula 256 can be removed as a unit and if necessary the incision through which the cannula 256 had been placed into the operating space can be enlarged.

After the device 151 has been removed from the cannula 256, the outer tubular assembly 151 is retracted onto the inner tubular assembly 154 as shown by the arrow 266 in FIG. 15F to expose the distal extremity of the tissue container assembly 221 after which the grasping instrument 251 can be removed. While holding the tubular member 171 of the inner tubular assembly 154 with one hand and grasping the twist cap 191 with the other hand, the twist cap 191 is removed by rotating in a counter-clockwise direction to release the proximal extremity 223 of the braided tube 222 and the proximal extremity 232 of the inner liner 231 permitting the user to grasp the tissue container assembly 221 in a region just beyond the flared portion to permit it to be pulled out of the inner tubular assembly 154 in the direction of the arrow 271 as shown in FIG. 15H. After the tissue container assembly 221 has been removed, it can be cut open with scissors (not shown) to examine the tissue specimen. Alternatively, the entire container assembly 221 with the specimen then can be shipped to a laboratory for analysis with the tissue specimen 261 intact with its liquids contained within the impervious inner liner 231.

Let it be assumed that it is desired to reutilize the tissue removal device after a tissue specimen has been collected in the manner hereinbefore described and after the tissue removal device has been sterilized. A replacement tissue container assembly 221 can be taken as shown in FIG. 15I and its proximal extremity introduced through the distal extremities of the tubular members 156 and 171. The distal extremities 158 and 173 are substantially flush with each other in this collapsed position. The proximal extremity of the tissue container assembly 221 is advanced as shown by the arrow 272 until it is beyond the proximal extremity of the tubular member 171. If necessary, a grasper can be utilized for pulling in the proximal extremity of the container assembly 221 into the bore 174 of the tubular member 171.

As soon as this has been accomplished, the twist cap 191 can be screwed onto the proximal extremity of the tubular member 171 by having the cylindrical protrusion formed by the tapered surface 198 on the wall 197 friction engaging the interior of the inner liner 231 and the braided tube 222 to firmly clamp them in place and secured to the proximal extremity of the tubular member 171 as shown in FIG. 15J. The device 151 is again ready for use and can be used in the manner hereinbefore described.

After the desired number of tissue specimens have been collected, the laparoscopic procedure can be completed in a conventional manner.

What is claimed is:

1. A laparoscopic tissue removal device for use with an introducer having a tubular housing, the laparoscopic tissue removal device comprising:

an elongate tubular member having a proximal end and a distal end;

an elongate tubular sheath having a proximal portion and a distal portion and a passage in communication with said elongate tubular member, the distal portion of said sheath being expandable from a compressed configuration and having an open distal end, said sheath secured to said elongate tubular member, the distal portion of said sheath extending beyond the distal end of said elongate tubular member, the proximal portion of said sheath removably secured to the proximal end of said elongate tubular member; and an outer sleeve comprising an elongate tube, said outer sleeve slidably mounted over said elongate tubular member, said outer sleeve being movable relative to said elongate tubular member and said sheath between a first position wherein the outer sleeve surrounds at least a part of the distal portion of said sheath to compress said expandable portion of said sheath and a second position wherein at least a part of the distal portion of said sheath extends out of the outer sleeve such that said sheath can expand.

2. The device of claim 1 wherein said sheath is formed of a woven braid material having an open weave construction.

3. The device of claim 2 further comprising an elastomeric material disposed in the woven braid material making the woven braid material impervious while permitting expansion of the expandable distal portion of said sheath.

4. The device of claim 1 further comprising an inner liner made of a flexible impervious material, said inner liner lining the distal portion of said sheath and secured to said sheath.

5. The device of claim 4 further comprising a drawstring secured near the distal extremity of said sheath to close said open distal end of said sheath.

6. The device of claim 1 further comprising a handle mounted on the proximal portion of said outer sleeve for slidably moving said outer sleeve relative to said elongate tubular member and said sheath.

7. A laparoscopic tissue removal device for use with an introducer having a tubular housing, the laparoscopic tissue removal device comprising:

an elongate tubular member having a proximal end and a distal end;

an elongate tubular sheath having a proximal portion and a distal portion and a passage in communication with said elongate tubular member, the distal portion of said sheath being expandable from a compressed configuration, the distal portion having an open end, the proximal portion of said sheath secured to the proximal portion of said elongate tubular member and the distal portion of said sheath extending beyond the distal end of said elongate tubular member, and;

an outer sleeve comprising an elongate tube, said outer sleeve slidably mounted over said elongate tubular member, said outer sleeve being movable relative to said elongate tubular member and said sheath between a first position wherein the outer sleeve surrounds at least a part of the distal portion of said sheath to compress said expandable portion of said sheath and a second position wherein at least a part of the distal portion of said sheath extends out of the outer sleeve and said sheath can expand.

8. The device of claim 7 further comprising a handle mounted on the proximal portion of said outer sleeve and a cap removably mounted on the proximal end of said elongate tubular member.

9. The device of claim 7 further comprising a cooperative stop between said elongate tubular member and said outer sleeve for preventing said outer sleeve from being completely withdrawn from said elongate tubular member.

10. A laparoscopic tissue removal device for use with an introducer having a tubular housing, the laparoscopic tissue removal device comprising:

an elongate tubular member having a proximal end and a distal end;

an elongate tubular sheath having a proximal portion and a distal portion and a passage in communication with said elongate tubular member, the distal portion of said sheath being expandable from a compressed configuration, the distal portion having an open end, the proximal portion of said sheath secured to said elongate tubular member and the distal portion of said sheath extending beyond the distal end of said elongate tubular member, and;

an outer sleeve comprising an elongate tube, said outer sleeve slidably mounted over said elongate tubular member, said outer sleeve being movable relative to said elongate tubular member and said sheath between a first position wherein the outer sleeve surrounds at least a part of the distal portion of said sheath to compress said expandable portion of said sheath and a second position wherein at least a part of the distal portion of said sheath extends out of the outer sleeve and said sheath can expand;

an inner liner having a proximal extremity, said inner liner lining at least the distal portion of said sheath, the proximal extremity of said inner liner being folded over the proximal end of said sheath; and a cap removably mounted on the proximal end of said elongate tubular member, said cap having a bore in communication with the interior of said inner liner and a seal with a hole therein and a removable plug for sealing said bore in said cap, said cap for removably securing said sheath and said inner liner to the proximal end of said elongate tubular member.

11. The device of claim 10 further comprising a grasping instrument extending through said hole in said seal, through said elongate tubular member and said outer sleeve, and through said inner liner, for grasping a mass of tissue and drawing said tissue into said inner liner.

12. The device of claim 11 further comprising a second seal, said second seal forming a substantially liquid-tight seal between the outer surface of said elongate tubular member and the inner surface of said outer sleeve.

13. The device of claim 12 further comprising a handle mounted on the proximal portion of said outer sleeve, and wherein said second seal is disposed on said handle.

14. A laparoscopic tissue removal device for use with an introducer having a tubular housing, the laparoscopic tissue removal device comprising:

an inner tubular member having a proximal end and a distal end;

an elongate tissue container having a proximal portion and a distal portion and a passage in communication with said elongate tubular member, the distal portion of said tissue container being expandable from a compressed configuration and having an open distal end, said tissue container secured to the proximal portion of said inner tubular member and the distal portion of said sheath extending beyond the distal end of said inner tubular member;

an outer tubular member slidably and coaxially mounted over said inner tubular member, said outer tubular member being movable relative to said inner tubular member and said tissue container between a first position wherein the outer tubular member surrounds at least a part of the distal portion of said tissue container to compress said expandable portion of said tissue container and a second position wherein at least a part of the distal portion of said tissue container extends out of the outer tubular member and said tissue container can expand;

an inner liner made of a flexible impervious material, said inner liner lining at least the distal portion of said tissue container and secured to said tissue container;

a handle mounted on the proximal potion of said outer tubular member for slidably moving said outer tubular member relative to said inner tubular member and said tissue container;

a cap removably mounted on the proximal end of said inner tubular member, said cap having a bore in communication with the interior of said inner liner and a seal with a hole therein in alignment with said bore in said cap; and a cooperative stop between said inner tubular member and said outer tubular member for preventing the outer tubular member from being completely withdrawn from said inner tubular member.

* * * * *